United States Patent
Shahi et al.

(10) Patent No.: US 6,312,698 B1
(45) Date of Patent: Nov. 6, 2001

(54) ANTI-FUNGAL FORMULATION ACTIVE AGAINST A BROAD SPECTRUM OF DERMATOPHYTOSES

(75) Inventors: Sushil Kumar Shahi; Amritesh Chandra Shukla; Anupam Dikshit; Ashok Kumar Bajaj, all of Allahabad; Anil Kumar Singh; Sushil Kumar, both of Lucknow, all of (IN)

(73) Assignee: Council of Scientific and Industrial Research, Rafi Marg (IN)

( * ) Notice: Subject to any disclaimer, the term of this patent is extended or adjusted under 35 U.S.C. 154(b) by 0 days.

(21) Appl. No.: 09/537,148

(22) Filed: Mar. 29, 2000

(51) Int. Cl.⁷ .................................................. A61K 35/78
(52) U.S. Cl. ........................................................ 424/195.1
(58) Field of Search .......................................... 424/195.1

(56) References Cited

PUBLICATIONS

Majumdar 1999 Indian Drugs 36(i): 1–14.
Singh et al. PAFA I Journal, Jan. Mar., 67–69, 1986.
Singh: Singh 1991, Insect Science Application 12(4):487–491.
Mehrotra et al. 1978, Ind.J. Pathol. Microbiol. 21: 131–134.
Banerjee Pasticha 1987, Ind.J. Microbiol. 5: 207–212.
Singh et al. 1983, Planta Medica 47(4) 256.
Konstantia et al. 1998 Agric. Food Chen. 46(5) 1739–1745.
Singh et al. 1986, MyKosen 29 (i) 37–40.
Dikshit et al. 1994, National Seminar on the Use of Traditional Medicinal Plants in Skin care. CIMAP Publication Lucknow, India p. 12.
Menghini et al., Plantes Medicinales et Phytotherapie 21(i) 36–42.
Beckstrom et al., CRC Handbook of Medicinal Mints (Aromathematics) Phytochemicals and Biological Activities, CRC Press 1996 USA pp. 419, 386 and 409.
Meyers 1927, J. Am. Med. Assoc. 89; 1834.
Dersarkission & Goodberry 1980, Studica Conserv 25–28.
Calderone et al. 1994; Jornal of Essential Oil Research 6(3) 279–287.
De Groot 1972, Mycologia 64: 862–870.
Caccioni et al. 1994, Journal of Essential Oil Research 6(2) 173–179.
Perry et al 1997, Phytochem 45 (8) 1605–1612.
Menphini et al. 1993; Riv. Ital. FPOS, 4, SP. No. 566–571.
Grover and Moore 1962, Phytopathology 52:876–880.
Shahi et al. 1999, Current Science 76(6) 836–839.
Garber and Houston 1956, Phytopathology 49: 449–450.
Roxburgh and Borrie, The English Language Book Soc. HK Lewis & Co. Ltd. XII Edition 1973.

Primary Examiner—Kevin E. Weddington
(74) Attorney, Agent, or Firm—BakerBotts, L.L.P.

(57) ABSTRACT

The invention provides a novel anti-fungal formulation active against a broad spectrum of dermatophytoses, said formulation comprising at least about 1% by weight of oil extracted from *Rabdosia melissoides* and one or more vegetable oils, solvents and additives.

31 Claims, No Drawings

ANTI-FUNGAL FORMULATION ACTIVE AGAINST A BROAD SPECTRUM OF DERMATOPHYTOSES

FIELD

The present invention provides a formulation based on the essential oil of plant *Rabdosia melissoides*, useful as a fungicide against a wide spectrum of dermatophytic fungi.

The formulation of the present invention has fungitoxic action against different dermatophytes and this property of the formulation is attributed to the fungicidal action of the volatile oil hydrodistilled from the medicinal plant *Rabdosia melissoides* and this is the first report of its utilization in these types of potent antimicrobial activities.

BACKGROUND

Dermatophytoses is a disease caused by a group of fungi known as dermatophytes. It is also known as ringworm or tinea and involves superficial infection of keratinized tissue of the skin of animals and human beings. Various species of three anamorpohic (asexual or imperfect) genera Epidermophyton, Microsporum and Trichophyton are commonly involved in these mycoses. The disease is prominent in tropical and subtropical countries due to their prevailing moisture and temperature regimes, and poses a therapeutic problem despite several antimycotic drugs available in the market.

Treatment of dermatophytoses is by use of topical or oral antifungal agents. There are 17 synthetic chemical compounds which are generally utilized (Majumdar 1999 Indian drugs 36(1): 1–14) for various superficial fungal infections but many of them produce adverse effect with fungistatic action only. Since herbal medicines have been reported to be comparatively safe and without any adverse side effect there has been revival of interest in the use of medicinal plants in developed and developing countries.

During the course of research, in an attempt prepare fungitoxic formulation from natural products the applicants have found that volatile oil of *Rabdosia melissodies* can be employed for controlling a number of dermatophytes.

The plant *Rabdosia melissodies* Benth. Syn. *Plactranthus melissoides* (Lamiaceae) is an important source of thymol. For the first time this species was introduced for cultivation by Central Institute of Medicinal and Aromatic Plants (Singh et al. PAFAI Journal, January March, 67–69, 1986). It is an herbaceous plant found to grow scattered in nature especially in Tarai region of Uttar Pradesh, India. The leaves and inflorescence of the plant on hydrodistillation yield essential oil which has been reported to exhibit repellent and fumigant properties for storage grain insects (Singh & Singh 1991, Insect Science Application 12(4) 487–491.

The basis on which the invention has been developed is the applicant's own finding that the essential oil of *Rabdosia melissoides* acts as a potent antidermatophytic agent. The oil showed broad range of antifungal activity completely inhibiting the mycelial growth of fungi such as *Microsporum abudouiniis, M. nanum, Trichophyton mentagrophytes* var *interdigitale, T. mentagrophytes* var *mentagraphytes, T. tonsurans, T. violaceum, Epidermophyton onvious floccosum, Microsporum gypseum* and *Trichophyton rubrum*, considered to be the most important dermatophytes (Mehrotra et al 1978, Ind. J. Pathol. Microbiol 21: 131–134; Banerjee Pasricha 1987, Ind. J. Med. Microbiol, 5: 207–212).

Twelve constituents have been identified in the essential oil of leaves of *Rabdosia melissoides* [Singh et al 1983, Planta Medica 47(4) 256]. They are -pinene, camphene, β-pinene, myrcene, -phellandrene, d-limonine, carene, -terpinene, p-cymene (25.4%), T-terpinene, thymol (19.8%) and carvacrol (15.4%). Thus thymol, p-cymene and carvacrol are the major constituents of the oil. There are quite a number of other plants viz. *Origanum vulgare, O. majorana, Thymus serpyllum, Thymus vulgaris* and *Trachyspermum ammi* syn *Carum copticum Satureja montana* and some Ocimum sp. which have been reported to contain thymol as a major constituent along with p-cymene and carvacrol. Among the oils of above plants, the oil of *Origanum vulgare* sp. *hirtum* has been reported to exhibit antifungal properties in vitro against human pathogens *Malassezai furfur* (yeast), *Trichophyton rubrum* (contains ginalool also) and *Trichosporum beigelli* [Konstantia et al 1998 J. Agric. Food. Chen. 46(5) 1739–1745). The oil showed promising results when tested on *T. rubrum* infected rats. The oil of *Trachyspermum ammi* contains 3 major constituents, thymol, carvacrol, and p-cymene, and has been reported to check growth of *Epidermophyton floccosum, Microsporum canis, Trichophyton mentagrophytes* in vitro. [Sing et al 1986; MyKosen 29(1) 37–40]. The oil of *T. ammi* has also been evaluated in the form of an ointment in human beings but it has been found to produce some adverse effects on the mammalian skin when applied locally. (Dixit et al. 1994 Traditional Medicinal Plants in Skin care CIMAP Publication, Lucknow, India p 12). The oils of *Thymus serphyllum* and *T. vulgaris* are reported to check the growth of *Candida albicans*. [Menghini et al 1987, Plantes Medicinales et Phytotherapie 21(1) 36–42].

Thymol, carvacrol and p-cymene have been reported to exhibit fungicidal activity (CRC Hand book of Medicinal Mints (Aromathematics) Phytochemicals and Biological activity, Stephen M. Beckstrom—Sternberg James A. Duke, CRC Press 1996 Printed in USA pp 419, 386, 409]. On further detailed literature survey it was found that thymol exhibits antifungal activity in vitro [Myers 1927, J. Am. Med Asso. 89 1834] and is effective as antifungal preservative [Dersarkission and Goodberry 1980, Studies Conserv 25–28] and checks the growth of honey bees pathogens, [Calderone et al. 1994, Journal of Essential Oil Research 6(3) 279–287]. p-Cymene has been found to check the growth of wood-habiting fungi *Trichoderma viridi* (De Groot 1972, Mycologia 64 862–870). While the carvacrol has been found to inhibit the germination and growth of vegetable post harvest pathogenic fungi (Caccioni et al 1994, Journal of Essential Oil Research 6(2) 173–179]. The essentials oil of *Kunzea ericoides* var. *liniaris* containing 31% p-cymene has weak antifungal activity (Perry et al 1997. Phytochem 45 (8) 1605–16012) which reveal that p-cymene is not useful for dermatophytoses and carvacrol up to 40% present in the oil of *Saturega montana* was found to inhibit the growth of only one species of Trichophyton and the nature of toxicity is also fungistatic (Menphini et al 1993 Riv. Ital FPOS, 4, SP. No. 566–71) for dermatophytoses further the *Satureja montana* oil was effective in 24–48 hour in 0.1 u ml/l while the oil of *Rabdosia melissoides* is effective in 80 minutes at the same concentration. The studies have shown the superiority of *Rabdosia melissoides* oil over thymol (Table 6).

So, it is very clear that p-cymene, carvacrol or thymol are not shown to be a good agent against dermatophytic fungi separately or in combinations present in various known oils but the combination of these, present in *R. melissoides* oil along with certain unidentified constituents played a synergistic fungicidal action, so the oil from the plant—*R. melissoides* is a potential novel source for cure of dermatophytoses and its formulation development is also a novelty.

Thus available information about the essential oils and plants having thymol, carvacrol and p-cymene as major constituents or in isolation have not been found to act as antifungal agents effective against a broad spectrum of cutaneous mycoses/dermatophytoses.

OBJECTS

The main object of present invention is to develop a herbal formulation(s) active against a broad spectrum of dermatophytic fungi.

Another object of the invention is to provide a formulation useful as a topical cream which smoothens the skin and allows slow absorption of the contents, thereby causing effective action which completely eliminates the infection by killing the fungi.

Yet another object of the invention is to provide an anti-fungal formulation containing the essential oil extracted from plant *Rabdosia melissoides* as its main active principle.

Yet another object of the invention is to provide an anti-fungal formulation which is commercially viable.

A further object of the invention is to provide a formulation which is stain-free.

Yet another object of the invention is to provide a cheap anti-fungal formulation compared to other synthetic preparations available in market.

Yet another object of the invention is to provide a formulation having quick action.

Yet another object of the invention is to provide a formulation in which the activity of ingredient is thermostable.

SUMMARY

The invention provides novel formulation containing the essential oil of *Rabdosia melissoides* effective as an anti-fungal agent against a wide spectrum of decmatophytic fungi. Further, the invention also provides a method for the treatment of skin disorders using the said novel formulation.

DETAILED DESCRIPTION

Accordingly, the invention provides novel anti-fungal formulation comprising about atleast 1% of oil extracted from *Rabdosia melissoides* and one more vegetable oils, solvents and additives. Preferably, the oil extracted from *Rabdosia melissoides* is in the range of 1 to 5% by wt. of the formulation.

The formulation is prepared by drop wise drop wise absorption of 1–5 ml of essential oil of the plant *Rabdosia melissoides* in 95–99 ml of the base material at 40–60° C. with constant stirring and cooling down to room temperature and further curing the preparation for 48 hrs. in closed glass vials.

In a preferred embodiment, the formulation of the present invention comprises 1% (v/w) of the oil obtained from aerial parts of *Rabdosia melissoides* wherein 1 ml oil is absorbed over the base made by mixing 25 gm stearyl alcohol and 74 gm propylene glycol at 60° C. over a water bath and cooling down the preparation with constant stirring upto the ambient temperature and finally curing it for 48 hours in closed glass vials.

In an embodiment of the present invention the base used may be prepared by mixing different concentrations of liquid paraffin to the melted mixture of petroleum jelly and natural wax like bees wax or carnauba wax.

In yet another embodiment, the formulation is in the form of a cream, gel, lotion, capsule or combinations thereof.

In an embodiment, the oil from *Rabdosia melissoides* is absorbed over mineral oil, animal oil or vegetable oil selected from white oil, cord liver oil, tallo oil, whale oil, seal oil, linseed oil, poppy oil, soya oil, sunflower oil, mustard oil and coconut oil to prepare the formulation in a lotion form.

In an embodiment, the cream, gel or lotion is prepared by absorbing the oil of *Rabdosia melissoides* over solvents selected from polyalcohols, alkylglycols such as ethylene glycol, propylene glycol and glycerol.

In yet another embodiment of the present invention the said composition has shelf life of more than 48 months.

In still another embodiment of the invention there is no need to add any antioxidant in the formulation as the active ingredient is rich in phenolic compounds.

In still another embodiment of the invention the oil in the preparation does not loose its activity upto temperature of 100° C.

In still another embodiment of the formulation may act as a moisturiser.

In still another embodiment of the invention, the formulation does not leave any stain on clothes.

In still another embodiment of the formulation the said preparation is ecofriendly and biodegradable.

Thymol carvacrol and p-cymene have been reported to have fungicidal activity against a broad spectrum of cutaneous mycoses/dermatophytoses.

Fungicidal is a word which is used to describe all compounds which kill fungus, either plant pathogen or animal pathogen. Since, oil containing compounds thymol, carvacrol and p-cymene have not been reported for killing the fungi causing dermatophytoses i.e. superficial infection of keratinised tissue of skin of animals and human beings, our invention for use of the natural oil having these constituents along with some unidentified compounds present in the oil is, novel. However, the oil of *Trachyspermum ammi* which have these three compound have been reported once for use in an ointment but produce some adverse effects. Whereas this oil i.e. of *R. melissoides* does not produce adverse effects and is utilized for this type of preparation for the first time. Further, other oils have been tested only with two species are general fungus while in this invention we have included a wide range of dermatophytic fungi which is essential to get the total picture of a product.

The invention is illustrated by the following examples which should not be construed to limit the scope of the present invention.

Development and Testing of Different Formulations

EXAMPLE 1

| | |
|---|---|
| Essential oil of *Rabdosia melissoides* | 1 ml |
| Glycerol IP | 99 ml |

The essential oil obtained by hydrodistillation of herbs of *Rabdosia melissodies* (1 ml) was absorbed drop wise over previously warmed (40° C.) glycerol over water bath with constant stirring, after the addition of total oil the mixture was kept at ambient temperature in closed glass vial for curing.

The preparation was effective.

EXAMPLE 2

| Essential oil Rabodosia melissodies | 1 ml |
| --- | --- |
| Linseed oil | 99 ml |

The essential oil of *Rabdosia melissodies* 1 ml was absorbed over warmed linseed oil as described in experiment example 1.

The formulation was very effective. However, the only drawback was that the smell of the linseed oil was dominating.

EXAMPLE 3

| Essential oil of Rabdosia melissodies | 1 g |
| --- | --- |
| Bees wax. | 55 g |
| Petroleum jelly white | 30 g |
| Liquid paraffin | 14 g |

The essential oil obtained from hydrodistillation of herbs of *Rabdosia melissodies* (1 gm) was absorbed over the previously prepared base by melting mixture of bees wax (55 gm), petroleum jelly (30 gm) and liquid paraffin (14 gm). The oil was absorbed drop wise over a water bath at 60° C. with occasional stirring. The mixture was kept in a closed glass vial and left for 48 hours for curing.

The ointment was very effective and it produces a feeling of having a sticky layer on the surface of the skin so its use is good preferably for the exposed parts of the skin which are thicker and where the ointment is absorbed slowly in a little long duration, further, if in case of severe infection such formulation will form a thin protective layer from the water and dust. In case of *tinea mannum* and *T. badis* infections.

EXAMPLE 4

| Essential oil of Rabdosia melissodies | 1 ml |
| --- | --- |
| Propylene glycol IP | 99 ml |

The essential oil obtained by hydrodistillation of herbs of *Rabdosia melissodies* (1 ml) was absorbed drop-wise over previously warm (50°) propylene glycol (99 ml) over a water bath with constant stirring after addition of total oil the mixture was left over water bath further for one hour in a tightly closed vial. Then the preparation was kept at ambient condition for 48 hrs. for curing.

The formulation was very effective and can be applied preferably for *tinea capits* and *tinea unguia* for skull and nail infection.

EXAMPLE 5

| Essential oil of Rabdosia melissoides | 1 ml |
| --- | --- |
| Propylene glycol IP | 74 gm |
| Stearyl alcohol | 25 gm |

The essential oil obtained by hydrodistillation of herbs of *Rabdosia melissoides* (1 ml) was absorbed dropwise with constant stirring in warm (60° C.) mixture of Propylene glycol (74 gm) and stearyl alcohol (25 gm). After addition of all *Rabdosia melissoides* oil the mixture was taken off from the waterbath and left to cool down to room temperature with constant stirring till the mixture become viscous. The preparation was kept for curing for 48 hrs.

This formulation gave very good effect in controlling the infection and produced smoothness to the skin. On applying slowly with finger it get absorbed in the skin leaving a creamy shining appearance to the skin. The preparation when clinically compared with other ointments commonly available in the market its efficacy was found to be better (Table 4).

For clinical response this cream was applied topically on human patients for the control of fungal infection (dermatophytoses) for three weeks two times daily, the patients were not allowed to take any other systemic or topical medicine. Patients of age group 8 to 40 years selected randomly and a group of 30 individuals was formed, Table 5 reveals the efficacy of the present formulation.

The similar creams were prepared by increasing concentrations of oil of *Rabdosia melissoides* but it was found that the effect was similar to the cream prepared by mixing 1% oil, however cream having upto 5% *R. melissoides* oil did not show any irritant activity on human beings (Roxburgh and Borie's method), further the cream with higher concentrations of *R. melissoides* oil may be useful to the infections of hard superficial surfaces like skull and nail.

The curative properties of oil of *Rabdosia melissoides* is due to some specific concentrations of the constituents present in the oil along with many minor unidentified constituents.

In vitro Studies of Antifungal Activities

For in vitro investigations, the minimum effective concentrations (MECs) of the oil were determined following minor modifications of poisoned food technique [Grover and Moore 1962, Phytopathalogy 52, 876–880); Shahi et al 1999, Current Science 76 (6) 836–839]. Minimum fungistatic and fungicidal concentrations of the oil were determined by the method of Garber and Houston 1959 [Phytopathalogy 49 449–450]. This was done by reinoculating the inhibited discs on sabouraud dextrose agar (SDA) medium in culture tubes. Inoculated culture tubes were incubated at 27±1° C. and the observations recorded on seventh day. While fungal growth indicated fungistatic activity, its absence denoted fungicidal action. The nature of toxicity of the oil was fungistatic at its minimum effective concentrations of 0.1 $\mu$l/ml, 0.2 $\mu$l/ml and 0.1 $\mu$l/mL against *E.floccosum, M. gypseum* and *T. rubrum* respectively (Table 1). The oil also inhibited heavy doses of inoculum. The minimum killing time was found to be 10, 20 and 10 seconds respectively with the pure oil against the three test pathogens (Table 2). However, at minimum fungicidal concentrations of 0.3 $\mu$l/mL against *E. floccosum*, 0.4 $\mu$l/mL against *M. gypseum* and 0.3 $\mu$l/mL against *T. rubrum* it required 80, 90 and 80 minutes respectively to kill the pathogens. The minimum killing time (MKT) of the oil was determined by mycelial disc killing technique (Shahi et al. 1999, Current Science 76 (6) 836–839]. Oil having 0.05 $\mu$l/ml to 0.2 $\mu$l/ml concentration produces fungi-static effect i.e. it stops the growth of fungus but when application is stopped, it reappears. While higher concentration i.e. 0.3 $\mu$l/ml to 0.4 $\mu$l/ml and above produces fungicidal effects i.e. it kills the fungus and reoccurrence of the disease do not take place. The oil was found to be thermostable up to 100° C., and it retained its fungicidal even after more than 48 months of storage. The oil exhibited wide range of activity inhibiting the mycelial growth of seven other fungi viz. *Microsporum, audouinii, M. canis, M. nanum, Trichophyton mentagrophytes,* Var. *interdigitale, T. mentagrophytes,* Var. *mentagrophytes, T. tonsurans* and *T. violaceum* (Table 3). On comparing the minimum fungistatic as well as fungicidal concentrations of the oil with that of the prevalent synthetic antifungal drugs, the oil was found to be more effective. Moreover, the oil did not exhibit any adverse effects on the mammalian skin up to 5% of concentration.

The expiry of toxicity of the oil was determined by storing them at room temperature and testing their antifungal activity at minimum effective concentrations (MCs) at regular intervals of 60 days up to 48 months following the usual poisoned food technique (Grover and Moore 1962). For determination of the effect of temperature, vials, containing 5 ml of oil each were kept separately. These were exposed to different temperatures viz. 40, 60, 80 and 100° C. in the incubator for one hour. The antifungal activity of the oil was then tested by poisoned food technique. Antifungal spectrum of the oil was determined at various concentrations viz 0.05, 0.1, 0.2, 0.3, 0.4 and 0.5 $\mu$l/ml, against other test pathogens by the usual poisoned food technique. Nature of toxicity of the oil whether fungistatic or fungicidal was determined by the method of Garber and Houston (Phytopathology 1959, 49 449–450) (Table 3).

The comparative study of the oil with some synthetic antifungal drugs was carried out by comparing MECs. The antifungal activity and nature of toxicity (i.e., fungistatic/fungicidal at their MECs) assayed following usual method as described earlier.

Clinical Trials

For in vivo investigations all the clinical trials were conducted on the patients (Out Patient Department) at Motilal Nehru Medicinal College, Allahabad (UP) by the method of Shahi et al. (1999) Current Science 76(6):836–39. Patients of either sex were diagnosed for either *tinea pedis, tinea corporis* or *tinea cruris* based on site of infection, the diagnosis was further confirmed by microscopic examinations of the scraping (from infected area) treated with 10% KOH. Patients showing *mycelium* and/or *conidia* were designated KOH positive. Only KOH positive cases were enrolled. Patients were examined just before the therapy was initiated and at the end of each week of 3 weeks of treatment. Although when the cutaneous fungal disease manifested itself in several body areas, all affected areas could be treatment but only one was selected and designated as the reference lesion. At each visit of the patient, the same reference lesion was scraped for fungal culture to identify the organism and for demonstration of presence of hyphae by microscopic examination of the scrapings which were covered with 10% KOH preparations. Signs and symptoms of inflammation as erythema, scaling, itching, maceration, vesiculation and pustulation were recorded as absent, mild, moderate, or severe. At each visit of the patient, overall clinical improvement was rated as worse, none, partial, significant or completely clear by comparing the conditions with those existing at the time of initial visit. Any adverse systemic or local reaction was noted at each visit and recorded as mild, moderate or severe. Satisfactory response with KOH-negative cases after third week were re-examined after one month relapse rate if any. To find out maximum tolerable concentrations (MTCs) for irritant activity, if any, of the oil by their topical application of human skin following the patch test method of Roxburgh and Borrie (The English Language Book Soc. H. K. Lewis and Co. Ltd. XII edition 1973). People of different sex in the age group of 10 to 30 years were selected randomly and a group of 30 individuals of each sex was constituted. Circular area sof 5 cm$^2$ on upper hairy and lower glabrous surface of palms and 3 cm$^2$ of neck region of each individual were first washed with distilled water followed by 70% ethyl alcohol and then allowed to dry for five minutes. Five drops of the graded concentrations of testing solution was applied to each individual separately. The volunteers were not allowed to wash the applied area. The qualitative observations were recorded after 24 hours of application.

TABLE 1

Minimum effective concentrations of the oil of *Rabdosia milissoides* against test pathogens (Poisoned food technique).

| | Mycelial Growth Inhibition (MGI %) | | |
|---|---|---|---|
| Concentrations ($\mu$l/mL) | *E. floccosum* | *M. gypseum* | *T. rubrum* |
| 0.4 | 100$^c$ | 100$^c$ | 100$^c$ |
| 0.3 | 100$^c$ | 100$^s$ | 100$^c$ |
| 0.2 | 100$^s$ | 100$^s$ | 100$^s$ |
| 0.1 | 100$^s$ | 71.0 | 100$^s$ |
| 0.05 | 78.2 | 59.3 | 74.0 |

$^s$fungistatic
$^c$fungicidal

TABLE 2

Minimum killing time of the oil of *Rabdosia milissoides* against test pathogens (Mycelial disc killing technique, Shahi et al. 1999 Current Science 76 (6) 838–839).

| | Fungal Growth Inhibition (FGI %) | | | | | |
|---|---|---|---|---|---|---|
| Minimum killing | *E. floccosum* | | *M. gypseum* | | *T. rubrum* | |
| time (MKT) | PO | MCC | PO | MCC | PO | MCC |
| 120 min. | 100 | 100 | 100 | 100 | 100 | 100 |
| 90 min. | 100 | 100 | 100 | 100 | 100 | 100 |
| 80 min. | 100 | 100 | 100 | 82.1 | 100 | 100 |
| 70 min. | 100 | 90.2 | 100 | 64.2 | 100 | 91.0 |
| 60 min. | 100 | — | 100 | — | 100 | 81.3 |
| 50 min. | 100 | — | 100 | — | 100 | 61.9 |
| 40 min. | 100 | — | 100 | — | 100 | — |
| 30 min. | 100 | — | 100 | — | 100 | — |
| 60 Sec. | 100 | — | 100 | — | 100 | — |
| 30 Sec. | 100 | — | 100 | — | 100 | — |
| 20 Sec. | 100 | — | 100 | — | 100 | — |
| 10 Sec. | 100 | — | 73.2 | — | 100 | — |
| 2 Sec. | 63.2 | — | 39.2 | — | 73.1 | — |
| 1 Sec. | 23.2 | — | 15.0 | — | 52.2 | — |

PO = pure oil
MCC = minimum fungicidal concentration

TABLE 3

Antidermatophytic spectrum of the oil of *Rabdosia milissoides*

| | Mycelial growth Inhibition at various concentration ($\mu$l/ml.) | | | | | |
|---|---|---|---|---|---|---|
| Fungi | 0.05 | 0.1 | 0.2 | 0.3 | 0.4 | 0.5 |
| *Microsporum audouinii* | 56.2 | 76.2 | 100$^s$ | 100$^s$ | 100$^c$ | 100$^c$ |
| *M. canis* | 46.3 | 82.3 | 100$^s$ | 100$^s$ | 100$^c$ | 100$^c$ |
| *M. nanum* | 50.2 | 91.3 | 100$^s$ | 100$^s$ | 100$^c$ | 100$^c$ |
| *Trichophyton mentagrophytes* var. interdigitale | 83.2 | 100$^s$ | 100$^s$ | 100$^c$ | 100$^c$ | 100$^c$ |
| *T. mentagrophytes* var. mentagrophytes | 51.0 | 76.3 | 100$^s$ | 100$^s$ | 100$^c$ | 100$^c$ |
| *T. tonsurans* | 76.9 | 100$^s$ | 100$^s$ | 100$^c$ | 100$^c$ | 100$^c$ |
| *T. violaceum* | 83.2 | 100$^s$ | 100$^s$ | 100$^c$ | 100$^c$ | 100$^c$ |

$^c$ = fungicidal
$^s$ = fungistatic

TABLE 4

Comparative efficacy of the formulation of *Rabdosia milissoides* with commercial antifungal drugs

| Oil and trade name of antifungal agents | Active ingredients | Minimum effective concentration (µl/ml.) | | | | | |
|---|---|---|---|---|---|---|---|
| | | *E. floccosum* | | *M. gypseum* | | *T. rubrum* | |
| | | MSC | MCC | MSC | MCC | MSC | MCC |
| Cream of present formulation | Essential oil | 0.1 | 0.3 | 0.2 | 0.4 | 0.1 | 0.3 |
| Dactrine | Miconazol Nitrate | 6.0 | * | 5.0 | * | 4.0 | * |
| Nizral | Ketoconazole | 0.5 | * | 5.0 | * | 4.0 | * |
| Tenaderm | Tolnaftate | 1.5 | * | 0.4 | * | 0.7 | * |
| Batrafine | Ciclopirox alamine solution | 0.3 | 1.0 | 0.1 | 0.5 | 0.3 | 0.5 |

MSC = minimum fungistatic concentration
MCC = minimum fungicidal concentration
* = remained static

TABLE 5

Patients showing clinical response of ointment prepared from the oil of *Rabdosia milissoides*

| Response | Percentage of patients showing clinical response for three weeks | | |
|---|---|---|---|
| | 1 | 2 | 3 |
| Worse | 0.0 | 0.0 | 0.0 |
| None | 0.0 | 0.0 | 0.0 |
| Partial improvement | 75.0 | 15.0 | 0.0 |
| Significant improvement | 25.0 | 70.0 | 40.0 |
| Complete clear | 0.0 | 15.0 | 60.0 |

The Main Advantages of the Present Invention are
1. Most of the topical creams available in the market are fungistatic and there is recurrence of the infection after discontinuance of the medicines. However, the present formulation was highly effective with fungicidal action where infection is completely eliminated and there is no recurrence of the infection.
2. The formulation has very long shelf life (>48 months).
3. There is no need of adding any antioxidant or preservative as the active ingredients in the oil are rich in phenolic components.
4. The formulation acts as a moisturiser and smoothens the skin surface thereby checking the itching of the infected part.
5. The activity of the oil is thermostable upto 100° C. so there is no need of storing under low temperature.
6. The formulation can be washed from the infected surface with water only so there is no need of soap or solvent to clean the infected part as the use of these may cause some adverse effects.

What is claimed is:

1. A novel anti-fungal formulation active against a broad spectrum of dermatophytoses, said formulation comprising atleast about 1% by weight of oil extracted from *Rabdosia melissoides*, and one or more of vegetable oils, solvents and additives.

2. A formulation as claimed in claim 1 wherein the oil is obtained from the aerial parts of *Rabdosia melissoides*.

3. A formulation as claimed in claim 1 wherein the formulation is in the form of a cream, ointment, gel, lotion, capsule or combinations thereof.

4. A formulation as claimed in claim 1 wherein the oil extracted from *Rabdosia melissoides* is in the range of 1–5% by wt. of the formulation.

5. A formulation as claimed in claim 1 wherein, a lotion is prepared by absorbing the oil of *Rabdosia melissoides* over mineral oil, animal oil or vegetable oil selected from white oil, cord liver oil, tallo oil, whale oil, seal oil, linseed oil, poppy oil, soya oil, sunflower oil, mustard oil and coconut oil.

6. A formulation as claimed in claim 1 wherein, cream or gel forms of the formulation is prepared by absorbing the oil of *Rabdosia melissoides* over solvents selected from polyalcohols, alkylglycols such as ethylene glycol, propylene glycol and glycerol.

7. A formulation as claimed in claim 1 wherein the base for preparation of various forms of the formulation is prepared by mixing 25 gm stearyl alcohol and 74 gm propylene glycol at 60° C. over a water bath and cooling down the preparation with constant stirring upto the ambient temperature and finally curing it for 48 hours.

8. A formulation as claimed in claim 1 wherein, the base for preparation of ointment form of the formulation is prepared by mixing liquid paraffin to the melted mixture of petroleum jelly and natural wax selected from bees wax and cornauba wax.

9. A formulation as claimed in claim 1 wherein, the formulation has a shelf life of more than 48 months.

10. A formulation as claimed in claim 1 wherein, the formulation is active against dermatophytic fungi selected from *Microsporum audouinii, M.canis, M.nanum, Trichophyton mentagrophytes* var. *interdigitale, T. mentagrophytes* var. *mentagrophytes, T. tonsurans, T. violaceum, Epidermophyton floccosum, Microsporum gypseum* and *Trichophyton rubrum*.

11. The formulation of claim 1 wherein the oil comprises -pinene, camphene, β-pinene, myrcene, -phellandrene, d-limonine, carene, -terpinene, p-cymene, T-terpinene, thymol, carvacrol or combinations thereof.

12. A method for the treatment of dermatophytoses comprising the steps of topical administration of the formulation as claimed in claim 1 at a concentration level ranging between 0.04 µl/ml to 0.5 µl/ml for a period of upto three weeks.

13. A method for the preparation of an anti-fungal formulation containing essential oil of *Rabdosia melissoides*, said method comprising the steps of absorbing drop wise 1–5 ml of essential oil of *Rabdosia melissoides* in 95–99 ml of the base material at 40–60° C. with constant stirring and cooling down to room temperature and further curing the preparation for 48 hrs. in closed glass vials.

14. A method of inhibiting the growth of or killing a broad spectrum of dermatophytic fungi comprising exposing the fungi to a formulation comprising oil extracted from *Rabdosia melissoides*.

15. The method of claim 14 wherein the genus of the dermatophytic fungi is selected from the group comprising Epidermophyton, Microsporum, and Trichophyton.

16. The method of claim 15 wherein the species of Epidermophyton is floccosum.

17. The method of claim 15 wherein the species of Microsporum is selected from the group consisting of *audouinii, canis, nanum,* and *gypseum*.

18. The method of claim 15 wherein the species of Trichophyton is selected from the group consisting of *mentagrophytes* var. *interdigitale, mentagrophytes* var. *mentagrophytes, tonsurans, violaceum,* and *rubrum*.

19. The method of claim 14 wherein the concentration of oil ranges from about 0.04 µl/ml to about 0.5 µl/ml.

20. The method of claim 14 wherein the formulation further comprises a base material.

21. The method of claim 20 wherein the formulation is prepared by (i) absorbing dropwise 1–5 ml of essential oil of *Rabdosia melissoides* in 95–99 ml of the base material at 40–60° C., with constant stirring, (ii) cooling down to a temperature ranging between 20–40° C., and (iii) curing for 48 hrs in closed glass vials.

22. The method of claim 20 wherein the base material comprises an organic solvent selected from propylene glycol, ethylene glycol, glycerol.

23. The method of claim 21 wherein the oil of *Rabdosia melissoides* is absorbed over mineral oil, animal oil or vegatable oil.

24. The method of claim 23 wherein the mineral oil, animal oil or vegatable oil is selected from the group consisting of white oil, cord liver oil, tallo oil, whale oil, seal oil, linseed oil, poppy oil, soya oil, sunflower oil, mustard oil, and coconut oil alone and mixtures thereof.

25. The method of claim 20 wherein the base material is prepared by mixing different concentrations of liquid paraffin to the melted mixture of petroleum jelly and natural wax like bees wax or carnauba wax to prepare an ointment.

26. The method of claim 14 wherein the formulation acts as a moisturiser and smoothens the skin surface thereby checking the itching of the infected part.

27. The method of claim 14 wherein the exposure of the fungi to the formulation occurs more than 48 months after the formulation was prepared.

28. The method of claim 14 wherein the fungicidal activity of the formulation is thermostable up to 100° C.

29. A novel synergistic anti-fungal formulation active against a broad spectrum of dermatophytoses, said formulation comprising from about 0.05 $\mu$l/ml to about 1% by weight of oil extracted from *Rabdosia melissodies,* and one or more of vegetable oils, and optionally solvents and additives.

30. A composition comprising oil extracted from *Rabdosia melissoides* at a concentration of at least about 0.05 microliter of oil per milliliter of composition.

31. A method for the treatment of dermatophytoses which comprises topical administration as claimed in claim 1 at a concentration level ranging between 0.04 $\mu$l/ml to 0.5 $\mu$l/ml either in the form of a lotion or a cream for a period of upto three weeks.

* * * * *

UNITED STATES PATENT AND TRADEMARK OFFICE
CERTIFICATE OF CORRECTION

PATENT NO. : 6,312,698 B1
DATED : November 6, 2001
INVENTOR(S) : Shahi et al.

It is certified that error appears in the above-identified patent and that said Letters Patent is hereby corrected as shown below:

Title page,
Item [56], References Cited, OTHER PUBLICATIONS,
Under "Calderone", "Jornal" should read -- Journal --
Item [73], Assignee, "Rafi Marg" should read -- New Delhi --

Column 1,
Line 17, "Dermatophytoses" should read -- Dermatophytosis --
Line 21, "anamorpohic" should read -- anamorphic --
Line 22, "Epidermophyton, Microsporum, and Trichophyton" should read
-- *Epidermophyton*, *Microsporum*, and *Trichophyton* --
Line 28, "dermatophytoses" should read -- dermatophytosis --
Lines 39 and 41, "*melissodies*" should read -- *melissoides* --
Line 57, "*abudouiniis*," should read -- *audouinii*, --

Column 2,
Line 1, "-pinene" should read -- $\alpha$-pinene --
Line 2, "-phellandrene" should read -- $\alpha$-phellandrene --
Line 3, "-terpinene" should read -- $\alpha$-terpinene --
Line 7, "*copticum Satureja*" should read -- *copticum, Satureja* --
Line 13, "*Malassezai*" should read -- *Malassezia* --
Line 14, "*Trichosporum beigelli*" should read -- *Trichosporon beigelii* --
Line 23, "(Dixit et al." should read -- (Dikshit et al. --
Line 50, "dermatophytoses" should read -- dermatophytosis --
Lines 55 and 67, "toses" should read -- tosis --
Line 56, "0.1 u ml/l" should read -- 0.1 µl/l --

Column 3,
Line 36, "decmatophytic" should read -- dermatophytic --
Line 42, "atleast" should read -- at least --
Line 47, "drop wise drop wise" should read -- dropwise --
Line 58, "upto" should read -- up to --

Column 4,
Line 3, "cord" should read -- cod --; and "tallo" should read -- tallow --
Line 18, "loose" should read -- lose --; and "upto" should read -- up to --
Line 21, "moisturiser" should read -- moisturizer --
Line 27, Thymol carvacrol" should read -- Thymol, carvacrol --
Line 32, "Since," should read -- Since --
Line 34, "dermatophytoses" should read -- dermatophytosis --
Line 35, "nised" should read -- nized --

UNITED STATES PATENT AND TRADEMARK OFFICE
CERTIFICATE OF CORRECTION

PATENT NO.    : 6,312,698 B1
DATED         : November 6, 2001
INVENTOR(S)   : Shahi et al.

Page 2 of 4

It is certified that error appears in the above-identified patent and that said Letters Patent is hereby corrected as shown below:

Column 4 cont'd,
Line 38, "is, novel." should read -- is novel. --
Line 39, "have" (both occurrences) should read -- has --
Line 40, "produce" should read -- produces --
Line 61, "*melissodies*" should read -- *melissoides* --; and "drop wise" should read -- dropwise --

Column 5,
Line 4, "*Rabodosia melissodies*" should read -- *Rabdosia melissoides* --
Lines 8, 19, 23, 43 and 47, "*melissodies*" should read -- *melissoides* --
Line 28, "drop wise" should read -- dropwise --
Line 35, "long" should read -- longer --
Line 37, "*tinea*" should read -- *Tinea* --; and "*T.badis*" should read -- *T. pedis* --
Line 49, "stirring after" should read -- stirring. After --
Line 55, "*tinea capits*" should read -- *Tinea capitis* --; and "*tinea unguia*" should read -- *Tinea unguium* --

Column 6,
Line 1, "Propylene" should read -- propylene --
Line 5, "become" should read -- became --
Line 8, "get" should read -- gets --
Line 15, "(dermatophytoses)" should read -- (dermatophytosis) --
Line 24, "upto" should read -- up to --
Line 29, "is" should read -- are --
Lines 37 and 41, "Phytopathalogy" should read -- Phytopathology --

Column 7,
Line 1, "*Microsporum,audouinii*" should read -- *Microsporum audouinii* --
Line 11, "(MCs)" should read -- (MECs) --
Line 19, "viz" should read -- viz. --
Line 44, "treatment" should read -- treated --
Line 65, "area sof" should read -- areas of --

Column 8,
Tables 1, 2 and 3, "*milissoides*" should read -- *melissoides* --

Column 9,
Table 4, "*milissoides*" should read -- *melissoides* --; and "antifugal" should read -- antifungal --

UNITED STATES PATENT AND TRADEMARK OFFICE
CERTIFICATE OF CORRECTION

PATENT NO. : 6,312,698 B1
DATED : November 6, 2001
INVENTOR(S) : Shahi et al.

It is certified that error appears in the above-identified patent and that said Letters Patent is hereby corrected as shown below:

Column 9,
Table 5, "*milissoides*" should read -- *melissoides* --
Line 48, "moisturiser" should read -- moisturizer --
Line 51, "upto" should read -- up to --
Line 60, "atleast" should read -- at least --

Column 10,
Line 6, "cord" should read -- cod --; and "tallo" should read -- tallow --
Line 18, "upto" should read -- up to --
Lines 20, 25 and 27, "wherein," should read -- wherein --
Line 24, "cornauba" should read -- carnauba --
Line 29, "*M.canis*" should read -- *M. canis* --; and "*M.nanum*" should read
-- *M. nanum* --
Line 35, "-pinene" should read -- ∝-pinene --; and "-phellandrene" should read
-- ∝-phellandrene --
Line 36, "-terpinene" should read -- ∝-terpinene --
Line 41, "upto" should read -- up to --
Line 56, "Epidermophyton, Microsporum, and Trichophyton." should read
-- *Epidermophyton, Microsporum,* and *Trichophyton.* --
Line 58, "Epidermophyton is floccosum." should read
-- *Epidermophyton* is *floccosum.*--
Line 60, "Microsporum" should read -- *Microsporum* --
Line 63, "Trichophyton" should read -- *Trichophyton* --

Column 11,
Line 11, "glycerol." should read -- and glycerol. --
Lines 14 and 16, "vegatable" should read -- vegetable --
Line 17, "cord" should read -- cod --; and "tallo" should read -- tallow --

Column 12,
Line 2, "moisturiser" should read -- moisturizer --

UNITED STATES PATENT AND TRADEMARK OFFICE
CERTIFICATE OF CORRECTION

PATENT NO.   : 6,312,698 B1
DATED        : November 6, 2001
INVENTOR(S)  : Shahi et al.

It is certified that error appears in the above-identified patent and that said Letters Patent is hereby corrected as shown below:

Column 12, con't
Line 11, "*melissodies,*" should read -- *melissoides,* --
Line 17, "dermatophytoses" should read -- dermatophytosis --
Line 20, "upto" should read -- up to --

Signed and Sealed this

Twenty-seventh Day of May, 2003

JAMES E. ROGAN
*Director of the United States Patent and Trademark Office*